United States Patent [19]

Gildenberg

[11] Patent Number: 5,423,832

[45] Date of Patent: Jun. 13, 1995

[54] METHOD AND APPARATUS FOR INTERRELATING THE POSITIONS OF A STEREOTACTIC HEADRING AND STEREOADAPTER APPARATUS

[76] Inventor: Philip L. Gildenberg, 3776 Darcus, Houston, Tex. 77005

[21] Appl. No.: 129,317

[22] Filed: Sep. 30, 1993

[51] Int. Cl.⁶ .............................................. A61B 19/00
[52] U.S. Cl. .................................................... 606/130
[58] Field of Search ................ 606/1, 130; 604/116; 128/653.1–653.5, 898

[56] References Cited

U.S. PATENT DOCUMENTS

| | | | |
|---|---|---|---|
| 3,508,552 | 4/1970 | Hainault | 606/130 |
| 3,841,148 | 10/1974 | Becker | 606/130 |
| 4,228,799 | 10/1980 | Anichkov et al. | 606/130 |
| 4,884,566 | 12/1989 | Mountz et al. | 606/130 |
| 5,171,296 | 12/1992 | Herman | 606/130 |

Primary Examiner—Stephen C. Pellegrino
Assistant Examiner—Glenn Dawson
Attorney, Agent, or Firm—Vinson & Elkins

[57] ABSTRACT

A method and positioning apparatus for interrelating the positions of a stereotactic headring and a stereoadapter apparatus is disclosed. The interrelation of these elements allow coordinates established for specific intracranial areas by the stereoadapter apparatus to be aligned with those established for the stereotactic apparatus whereby diagnostic measurements made on the intracranial areas utilizing the stereoadapter apparatus may be used for purposes of intracranial treatments performed utilizing the stereotactic apparatus.

20 Claims, 9 Drawing Sheets

METHOD AND APPARATUS FOR INTERRELATING THE POSITIONS OF A STEREOTACTIC HEADRING AND STEREOADAPTER APPARATUS

BACKGROUND OF THE INVENTION

1. Field of the Invention

This invention relates to the field of brain surgery and other intracranial procedures performed on humans and, more specifically, to methods and apparatus for interrelating the positions of noninvasive stereoadapters used in performing presurgical diagnostic procedures and invasive stereotactic headring apparatus used in performing surgical, or other treatment, procedures.

2. Description of the Prior Art

Procedures which involve surgery, radiation or other procedures performed on the brain or other intracranial structures are especially hazardous for the patient, because of the extreme sensitivity of brain tissues, the difficulty in identifying and accessing the particular portion of the brain upon which a procedure is to be performed, and the danger of damaging brain tissues which overlie or surround the portion upon which the procedure is to be performed. The desire for precisely locating and accessing interior portions of the brain and other intracranial structures have lead to the development of the neurosurgical subspecialty of stereotactic surgery or "stereotaxis."

Stereotaxis ordinarily involves the use of an external apparatus attached to the patient's skull during presurgical diagnostic procedures and during surgical procedures. The apparatus provides a grid or framework in fixed position relative to the patient's skull which may be used to establish a coordinate system for locating, in a reproducible manner, the precise position of a lesion or other area within the intracranial area. The fixed framework also provides a structure external to the skull to which measuring devices, surgical instruments and the like can be attached and, by appropriate manipulation, positioned so they can be introduced to exact points within the intracranial structure. Surgical or other procedures then can be performed at an exact, predetermined, point within the brain or other tissue. The object of such devices is, ultimately, to permit safe impact at a predetermined location within the intracranial space for purposes such as excision, surgical biopsy, placement of catheters, installation of devices, removal of cysts, tumors or hematomas, or may involve focusing or direction of laser beams, radiation, magnetism or the like for diagnostic or treatment purposes.

The development of CAT scan technology, magnetic resonance imaging (MRI), angiography, digital subtraction angiography (DSA) and similar diagnostic procedures for producing images of structures contained within tissue has been applied to the field of stereotaxis to produce image-directed stereotaxis. A stereotactic apparatus is used in conjunction with advanced diagnostic imaging procedures to produce internal tissue images keyed to a cartesian or polar coordinate system. When the same stereotactic apparatus is utilized during surgery, it is possible to access a precise position inside the brain identified on the diagnostic images on the basis of the same coordinate system. Such image directed stereotactic procedures involve, generally, the steps of:

(1) establishing a stereotactic space incorporating all areas of the cranial structure under investigation by means of a rigid external framework positioned in fixed relationship to the skull;

(2) performing diagnostic imaging procedures with the framework in place, so that any lesion or other intracranial structure identified by the imaging procedure can be located in precise relationship to the fixed external framework and its position recorded on the basis of a coordinate system related to the stereotactic framework; and (3) utilizing the same external stereotactic framework and coordinate system during the surgical procedure to guide the surgical instruments, etc., to the precise location inside the cranium where a procedure is to be performed.

Although various stereotactic framework systems are in use throughout the world, the most popular systems are the Radionics Brown-Roberts-Wells (BRW) stereotactic system, the Cosman, Roberts and Wells (CRW) system, and the Elekta Instruments Leksell stereotactic system. The BRW, CRW, Leksell and other systems utilize an external headring which is rigidly attached to the patient's skull by means of four extensible pins, a localizing device with a plurality of vertical and inclined rods which may be attached to the headring during diagnostic procedures and which, in conjunction with computer software developed for the system, can translate CAT scan, MRI, etc., diagnostic imaging information produced with the headring and localizing device in place into X, Y and Z coordinates for any point within the stereotactic space. For the surgical procedure, the fixed headring is left in place, but the localizing device is removed and an arc or other surgical instrument placement device is attached to the headring which permits placement of a probe or other surgical instrument at any point in the intracranial space defined by the X, Y and Z coordinates. For ease of reference, all such stereotactic systems which use an external headring adapted to be rigidly and invasively attached to a patient's skull are referred to herein as "BRW/CRW."

A more detailed explanation of the prior art technology in this area may be obtained from various publications such as, for example, STEREOTACTIC BRAIN BIOPSY, P. T. Chandrasoma, M.D., and Michael L. J. Apuzzo, M.D. (Igaku-Shoin Medical Publishers, Inc. 1989); Heilbrun, M. P. (ed): STEREOTACTIC NEUROSURGERY, Baltimore, Williams & Wilkins, 1988; Lunsford, L. D. (ed): MODERN STEREOTACTIC NEUROSURGERY, Boston, Martinus Nijhoff Publishing, 1988.

Since stereotactic procedures have become increasingly important and widely used in the neurosurgical management of brain tumors and arteriovenous malformations, additional applications for the techniques are being developed. Recent advances include the use of stereotactic techniques in conjunction with linear accelerator therapy for tumor and arteriovenous malformation (AVM) irradiation, and fractionated radiotherapy for the treatment of deep-seated, surgically inaccessible brain tumors. The key to these developments has been the precision with which stereotaxis allows the surgeon to approach intracranial lesions or other areas, regardless of their size or location.

Until recently, for patients undergoing stereotactic procedures, it was necessary that all preoperative imaging procedures be performed on the day of surgery, because localization of a lesion or other intracranial structure was dependent upon extremely precise calculations done with the stereotactic headring in place. Since even the slightest variation in the position of the headring relative to the CAT scan, angiographic study, MRI imaging, etc. would negate the accuracy of the system, it was not possible for the ring to be removed until all the necessary components of the treatment had been completed. Unfortunately, this meant that some patients who required multiple pre-operative studies would be seen early in the morning of the procedure, have the fixed headring applied, spend the better part of the day having imaging studies done with the headring in place, and then begin the operative procedure itself in the late afternoon or evening. This was not only very stressful for the patient, but created difficult scheduling problems for the various medical services and personnel involved.

However, a device recently has been developed by Lauri Laitinen[1] and tested by Dr. Marwan Hariz[2] in Sweden. The Laitinen device, known as the "Laitinen stereoadapter," is noninvasive and is removably attached in an exactly reproducible position to the patient's head by reference to the patient's nose bridge and ears, so that it can be applied, removed and reapplied precisely. The Laitinen stereoadapter incorporates fiducial markers which can be related to CAT scans, magnetic resonance images, DSA or other images to establish an intracranial coordinate system. Since the device also can be applied, removed and reapplied substantially precisely, stereotactic coordinates can be obtained at the time of surgery, with full confidence that the position of the patient's head at the time of surgery is exactly where it was relative to the pre-operative imaging studies. Using the Laitinen stereoadapter, a patient could, for example, have a CAT scan done one day, an angiogram done another day, and the actual surgical procedure performed on a third day.

[1] Laitinen, L., Liliequist, B., Fagerlund, M. and Erikson, A. T.: An adapter for computer tomography-guided stereotaxis. Surg. Neurol. 23:559–566, 1985. Laitinen, L.: The Laitinen System. IN: Lunsford, L. D. (ed): Modem Stereotactic Neurosurgery, Boston, Nijhoff, 1988, pp. 99–116.
[2] Hariz, M. I.: A Non-invasive Adaptation System for Computed Tomography-Guided Stereotactic Neurosurgery. University of Umea (Sweden), 1990. Hariz, M. I.: Clinical Study on the Accuracy of the Laitinen CT-Guidance System in Functional Stereotactic Neurosurgery. Stereo. Funct. Neurosurg. 56:, 1991.

The Laitinen stereoadapter is compatible with the Laitinen stereotactic system (stereoguide), which utilizes a fixed external arcuate structure similar to a stereotactic headring for supporting surgical and measuring instruments, etc., at the time of surgery. The Laitinen external arc is attached to the patient's skull by means of extensible pins, and keys off of the stereoadapter, to assure accurate placement. Once the fixed external arc is in place, the stereoadapter is removed. Imaging or other diagnostic procedures performed using the Laitinen stereoadapter then identify intracranial structures on the basis of the same coordinate system utilized by the Laitinen system fixed external arc during surgical procedures.

The development of the Laitinen technology has been an important advance in stereotactic surgery for users of the Laitinen stereotactic system, most of whom are in Europe. However, the Laitinen stereoadapter is not compatible with BRW/CRW type stereotactic systems which are more prevalent in the United States. This is in part because the Laitinen and BRW/CRW systems use different baselines for the axes of their coordinate systems and because the BRW/CRW headrings cannot be sufficiently accurately positioned with respect to the Laitinen stereoadapter by any prior art means.

SUMMARY OF THE INVENTION

Accordingly, the primary object of the present invention to provide a method and apparatus by which the advantages of the noninvasive stereoadapter apparatus may be utilized during presurgical diagnostic procedures and invasive-type fixed BRW/CRW stereotactic devices may be used during surgical or radiosurgical procedures, with full assurance that the coordinates established for intracranial structures during the diagnostic procedures are reproducible during surgical or radiotherapeutic procedures.

A further object is to provide such a system in which the existing Laitinen stereoadapter apparatus may be utilized for diagnostic procedures and existing BRW/CRW stereotactic headring devices may be used during surgical procedures on the same patient.

A more specific object is to provide a mechanical device for interrelating in reproducible fashion the position of a Laitinen stereoadapter apparatus on a given patient to the position of a BRW/CRW stereotactic headring on the same patient, with the Laitinen and BRW/CRW coordinates substantially exactly aligned, so that diagnostic measurements obtained utilizing the Laitinen stereoadapter may be used for surgery performed with the BRW/CRW headring in place.

As shown more fully below, such objects and advantages are accomplished by the provision of a positioning device having means for exact alignment with the Laitinen stereoadpater, as well as means for mechanical connection with the BRW/CRW stereotactic headring, so that the stereotactic headring may be positioned in precise and known relationship to the stereoadapter. The positioning device of the present invention is dimensionally configured so that, when the BRW/CRW headring is positioned utilizing such device, the coordinate systems of the Laitinen stereoadpater and BRW/CRW headring will align substantially precisely, by which is meant within about one millimeter, plus or minus. Diagnostic measurements made with one system then may be used for surgical procedures performed using the other system.

BRIEF DESCRIPTION OF THE DRAWINGS

These and other objects and advantages of the present invention will be apparent to those skilled in the art from the following disclosure and description of a preferred embodiment of the invention and from the accompanying drawings, in which like numerals indicate like parts, and in which.

DETAILED DESCRIPTION

In the following detailed description of a preferred embodiment of the present invention, the terms "stereoadapter" and "stereoadapter apparatus" are used to refer both to the Laitinen stereoadpater apparatus disclosed, as well as to any similar stereotactic device which is substantially noninvasive, which may be placed, removed and replaced on the patient's head in a substantially reproducible position and which provides or positions fiducial means for establishing an intracranial measurement and coordinate system for diagnostic imaging purposes. The term "stereotactic headring" is used to refer both to the BRW/CRW-type headring illustrated, as well as to the Leksell and any other stereotactic device which is designed to be rigidly attached to a patient's head by means of invasive pins or the like which penetrate the outer tissues and engage the bony structure of the skull.

Figure 1:
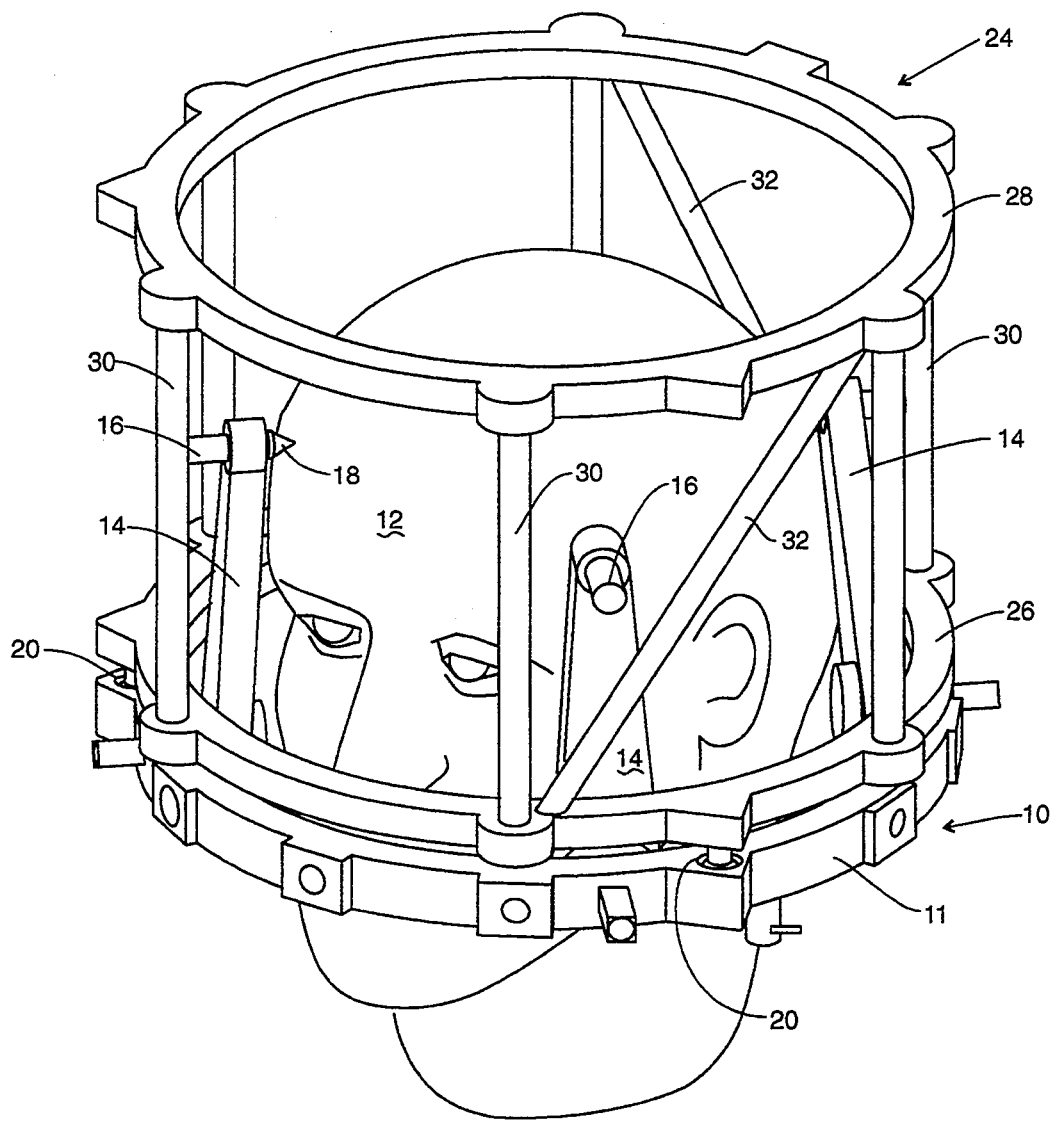
FIG. 1 (prior art) is an isometric view illustrating a BRW/CRW-type stereotactic headring attached to a patient's skull, with a localizer ring attached to the headring.

Referring now to FIG. 1, there is shown a BRW/CRW-type stereotactic headring 10 disposed around the outside of a patient's head 12. The headring comprises an annular base 11, formed of metal. Four vertical brackets 14 extend upward from the inside diameter of the base 11. Four adjustable pins 16 are threadedly engaged with the upper portions of the brackets 14. The pins 16, when rotated relative to the brackets 14, extend inwardly to engage the patient's skull, or retract outwardly to disengage from the patient's skull. The pins 16 have pointed tips or ends 18 which, when the pins are extended inwardly, penetrate the outer tissue of the patient's head 12 and engage the bone of the skull so as to rigidly and invasively affix the headring 10 to the skull. The pin tips or ends 18 may be removable and replaceable so as to reduce the possibility of spreading infection from one user of the headring apparatus to the next. Also, in certain applications, where rigid positioning of the headring is less critical, noninvasive pads may be substituted for the pin tips 18, which permits the headring 10 to be engaged around the patient's head in a noninvasive manner.

The headring 10 includes means for attaching to it other appliances used in stereotactic procedures. As shown, these comprise a plurality, ordinarily three, of recessed ball sockets 20 into which the ball-type connectors of compatible stereotactic appliances may be received. Spindles 22 extending downwardly from the underside of the headring 10 are connected to internal means (not shown) in the headring base 11 for locking in place ball-type connectors received in the sockets.

In prior art FIG. 1, the stereotactic headring 10 is supporting a localizing device 24 used for establishing a coordinate system and measurement reference for diagnostic procedures. The localizing device 24 includes a lower ring 26 and upper ring 28, both shaped to conform to the base 11 of the stereotactic headring 10. The rings 26 and 28 are interconnected by six vertical bars 30 and three inclined bars 32. Supports 34 extend downwardly from the bottom of lower ring 26 and terminate in ball connectors which are adapted to be received within the ball sockets 20 of the headring 10, so that the localizing device can be removably rigidly attached to the headring 10.

When diagnostic scanning procedures such as magnetic resonance imagining ("MRI") or computerized axial tomography ("CAT scan") or the like are performed on a patient's head with the localizing device 24 in place, the vertical and inclined bars 30, 32 provide fixed indicia (fiducials) against which measurements can be made and relative to which a coordinate system can be established for the cranium and intracranial areas. In conjunction with existing computer software developed for the system, the diagnostic images produced from the CAT scan, MRI, etc., performed with the localizing ring in place will provide X, Y and Z coordinates (or, in some applications, polar coordinates) for any portion of the patient's skull, brain or other tissue within the cranium which is to be investigated or treated. Such systems make it possible, for example, to identify the location of a tumor, or the like, within the patient's brain by X, Y and Z coordinates which define the position of the tumor, as well as its points of greatest extension within the brain tissue, etc. Since the localizing device 24 is rigidly attached to the headring 10, which in turn is rigidly attached to the patient's skull 12, the coordinates of diagnostic measurements made utilizing the localizing device 24 may be used directly as coordinates for later surgical, or other treatment, procedures performed utilizing other appliances or instruments rigidly attached to the headring 10 as long as the headring remains attached in position to the patient's head (FIG. 1). As used in this patent, the term "diagnostic procedure" is used broadly and encompasses imaging, visualizing and localizing procedures used for diagnosis and/or treatment of cranial and/or intracranial structures.

Figure 2:
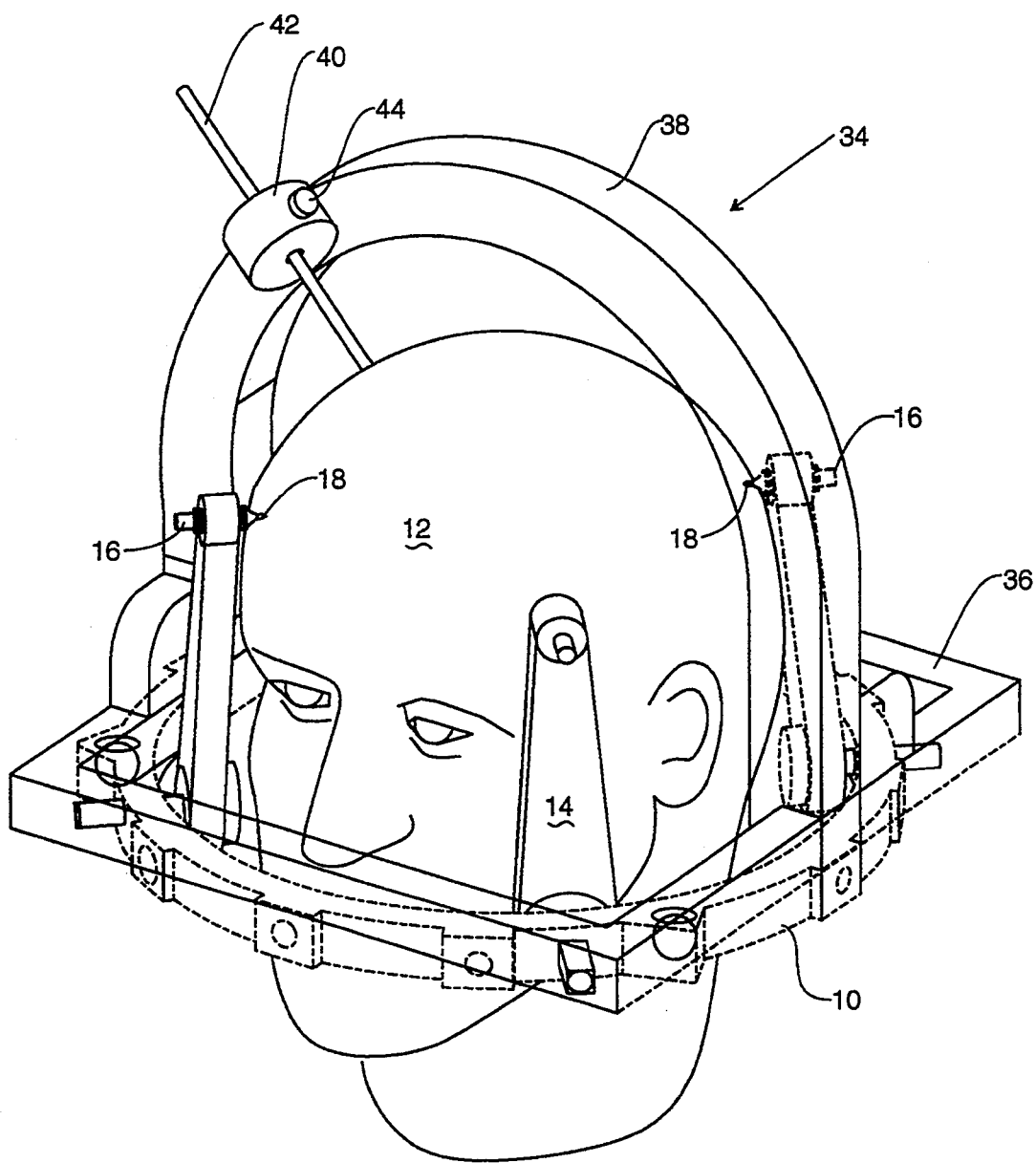
FIG. 2 (prior art) is a view similar to FIG. 1, but with the localizer ring removed and an instrument positioning are attached to the headring, which is shown partially in phantom lines in FIG. 2 for greater clarity.

FIG. 2 illustrates the BRW/CRW-type headring 10 still attached to the patient's skull but with the localizing device 24 removed and replaced by a surgical appliance holder 34. The appliance holder 34 comprises a base portion 36 attachable to the stereotactic headring 10 by means of ball-type connectors receivable in the headring sockets 20. An are 38 is mounted on the base 36 and includes a bracket 40 which may be used for holding and positioning a surgical appliance, such as the probe 42 illustrated. A set pin 44 locks the probe in position in the bracket 40. As is well known to those skilled in the art, the positioning of the supporting arc 38 and bracket 40 are adjustable, and all such parts, as well as the probe 42, are suitably calibrated, so as to permit any desired portion of the patient's brain to be accessed at a known coordinate location utilizing the device. Many other attachments, appliances and instruments are available and used in the BRW/CRW-type stereotactic systems presently commercially available. All of such attachments, appliances and instruments are configured and calibrated so as to use, for surgical purposes, the same coordinates for intracranial tissues established during diagnostic scanning procedures performed with the localizing device 24, or a similar fiducial device, mounted on the headring 10 while the headring 10 is rigidly attached to the patient's skull.

All of such systems now in use have the drawback that, in order for the coordinate system utilized in surgery to be the same as that established and utilized during diagnostic procedures, both the diagnostic procedures and the surgical procedure must be performed after the headring 10 has been attached to the patient and before it has been removed. Otherwise, there could be no assurance that the headring was replaced later in exactly the same position in which the diagnostic measurements were made. Because of the size and cumbersomeness of the headring, as well as the fact that it is invasively placed on the patient's head, as a practical matter this mandates that all diagnostic and surgical procedures be performed in one day.

Figure 3:
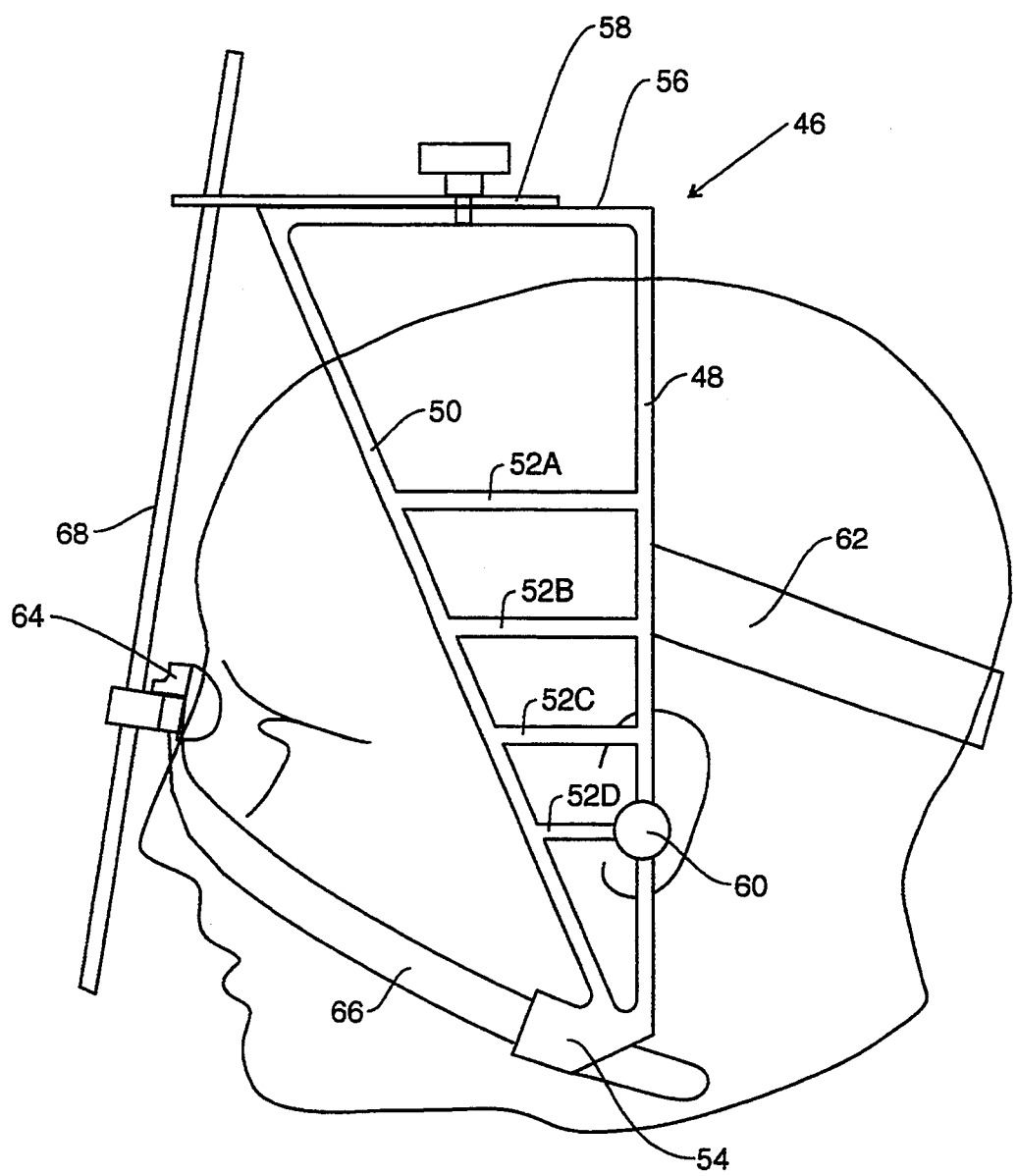
FIG. 3 (prior art) is a view in side elevation of a patient's head with the Laitinen stereoadapter apparatus positioned thereon.

Referring now to FIG. 3, there is shown the Laitinen-type stereoadapter 46 which may be securely positioned a patient's head in a noninvasive manner for diagnostic imaging purposes. The Laitinen stereoadapter includes fiducial means for establishing a coordinate and measurement system in conjunction with the diagnostic procedures. Such fiducial means are provided by pairs of vertical and inclined bars 48, 50 disposed on each side of the patient's head, and interconnected by a plurality of horizontal bars 52A-D extending between the vertical and inclined bars. The bars 48, 50 are also connected at their bases by brackets 54 and at their tops by horizontal bars 56, which also may form a part of the fiducial grid. The bars of such fiducial grid preferably are formed of plastic and the entire grid may, if desired, be cast as a unit. A pair of such fiducial grids are provided, one on each side of the patient's head, and are joined by a horizontal metal plate 58 extending between and connected to them.

Means for positioning the Laitinen stereoadapter on the patient's head are provided by two ear plugs 60 on the two vertical bars 48, a back head strap 62 attached to the vertical bars 48, a nose pad 64 supported by a front bracket 66 and a brace 68 extending between the nose pad 64 and plate 58. All of such attachment means are adjustable, so that the fiducial grids may be positioned on the patient's head with the vertical bars 48 in substantially vertical position and with the horizontal bars 52 substantially in horizontal position with respect to the diagnostic imaging apparatus (not shown) for purposes of establishing the measurement and coordinate system used in the diagnostic imaging procedures. All of such support means for the Laitinen stereoadapter also are calibrated so that the adapter may be removed, after performing a diagnostic procedure, and later replaced on the same patient in substantially exactly the same position as before.

Figure 4:
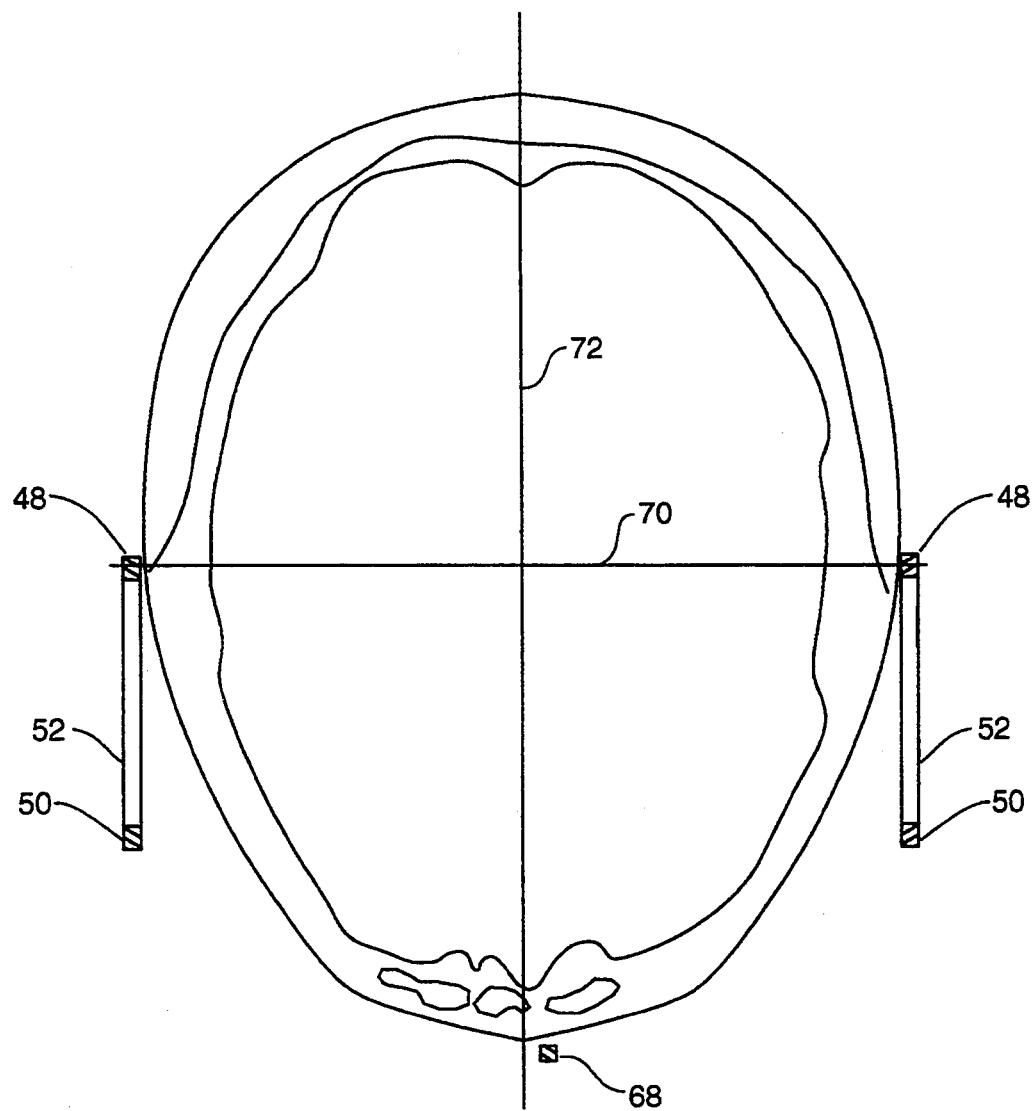
FIG. 4 (prior art) represents a planar graphic image of the patient's head, of the type which might be produced by a diagnostic imaging system, and illustrates the manner in which the fiducial indicia of the Laitinen stereoadapter permits cranial measurements for a coordinate system.

Referring to FIG. 4, there is illustrated a graphic image of the type which might be produced by a CAT scan or MRI imaging system, with the Laitinen stereoadapter in place. The existing computer software used in connection with the system produces a graphic image at any desired location, and overlays a measurement grid represented by the X and Y axes 70, 72 shown. So that intracranial areas may be identified in three dimensions, the computer-generated coordinate system also includes a Z axis (not shown) but extending perpendicular to the intersection of the X and Y axes shown. In each graphic image produced at any location along the Z axis, the vertical bar 48 and inclined bar 50 of the Laitinen stereoadapter would appear in cross section as small rectangles, as would a cross section of the front support bar 68. Since the inclined bar 50 is farther away from the vertical bar 48 the higher one moves on the Z axis, the distance between the cross sections of the vertical and inclined bars is utilized to confirm the Z axis measurement for each displayed graphic image. The position of any tissue along the X and Y axes can be determined with reference to the X axis line extending between the vertical bars 48 and the Y axis perpendicular to and bisecting such line. A surgeon utilizing the graphic images thus can identify the location and extent of any point within a lesion, tumor, or other structure by its respective X, Y and Z coordinates and thus know the precise location inside the brain which must be accessed to perform the desired procedure on the tumor, etc., assuming the same coordinate system is available during the surgical procedure as was used during the diagnostic procedure.

Figure 5:
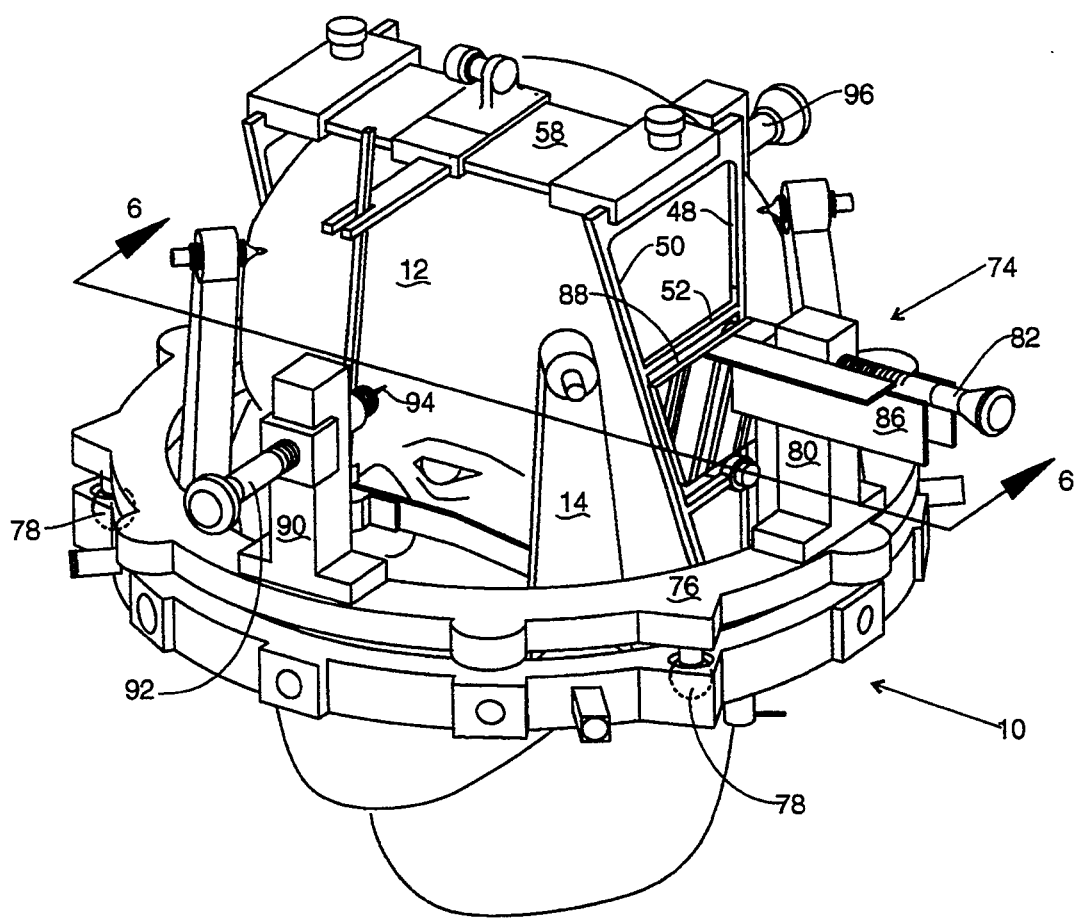
FIG. 5 is an isometric view of a patient's head fitted with a Laitinen stereoadapter apparatus as well as a BRW/CRW-type headring and with the positioning device of the present invention disposed between and interrelating the positions of the Laitinen stereoadapter and BRW/CRW headring.
Figure 6:
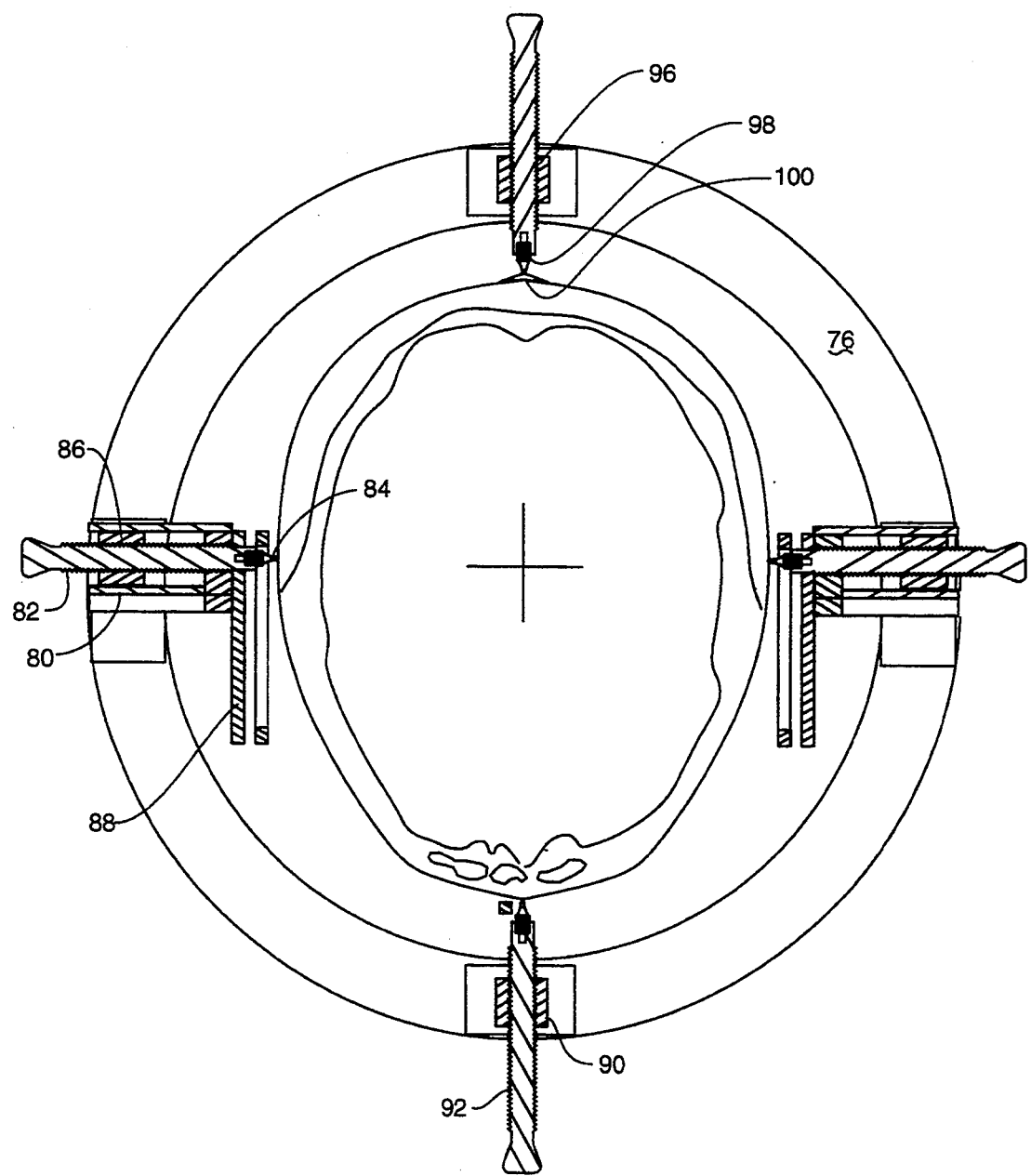
FIG. 6 is a plan view partly in section taken along line 6—6 of FIG. 5 and illustrating details of the positioning apparatus in accordance with the present invention (and from which portions of the Laitinen stereoadapter an BRW/CRW-type headring have been omitted for purposes of clarity)

Referring now to FIGS. 5 and 6, there is illustrated the positioning apparatus 74 in accordance with the present invention which may be used for interrelating the positions of a noninvasive stereoadapter apparatus and an invasive stereotactic headring. Such device 74 comprises a base ring 76 having three ball-type connectors 78 receivable within the ball sockets 20 of the BRW/CRW headring in the same manner as the localizer device and appliance holder discussed above. Attached to and extending upwardly from the base ring are two vertical brackets 80, one bracket being positioned on each side of the patient's head. The brackets 80 support elongated threaded pins 82 which terminate in removable points 84, similar to the removable ends of pins 16 discussed in connection with the BRW/CRW headring. The pins 82 are adjustable, by means of such threads, toward or away from the patient's head. Each bracket 80 also supports a horizontal slide mechanism 86 and scale to indicate the position of each pin 82. On the inside end of each horizontal slide mechanism is positioned a vertical trapezoidal plate 88 configured to conform to the trapezoidal area defined by the intersection of the topmost horizontal bar 52A with the vertical bar 48 and inclined bar 50 on the stereoadapter apparatus. The upper edge of horizontal bar 52A, the rear edge of vertical bar 48 and the forward edge of inclined bar 50 on the Laitinen stereoadapter 46 thus serve as alignment indicia with respect to which the two trapezoidal plates 88 are aligned.

A third vertical bracket 90 on the front of base ring 76 mounts a threaded pin 92 which also is adjustable, by means of such threads, toward or away from the patient's head 12. Pin 92 terminates in a replaceable point 94. A fourth vertical bracket 96 is provided on the back of base ring 76, opposite the bracket 90, and mounts a threaded adjustable pin 98 which terminates in a replaceable blunt support pad 100 to apply counterpressure to prevent movement of the adapter once the threaded pin 92 is secured.

In utilizing the positioning apparatus 74, the patient first is fitted with the stereoadapter apparatus 46 which previously would have been used in performing diagnostic imaging on the patient. The positioning apparatus 74, with the stereotactic headring 10 attached thereto, then is lowered in surrounding relationship to the stereoadapter apparatus 46 on the patient's head. The initial positioning of the apparatus 74 with respect to the Laitinen stereoadapter 46 is made by extending the two threaded pins 82 symmetrically toward the patient's head until they are received within the fight angle formed by the lower edge of horizontal bar 52A and the front edge of vertical bar 48 on the Laitinen stereoadapter. The two threaded pins 82 thus serve as an initial alignment means for the positioning apparatus 74. With the two pins so positioned relative to the Laitinen stereoadapter, the pins are further rotated to cause their points 84 to penetrate the patient's scalp and engage the bone of the skull, with both pins extended an identical distance as indicated on the calibration scales. This provides sufficient mechanical support for the positioning apparatus 74 and headring 10 carried by it and provides an initial vertical alignment of the positioning apparatus 74 relative to the Laitinen stereoadapter 46. Angular alignment then is provided by the two trapezoidal plates 88, which are positioned in close proximity to, and properly aligned with, the rear edge of the vertical bar 48 and forward edge of the inclined bar 52 on the Laitinen stereoadapter, which places the positioning apparatus in proper angular alignment with respect to the Laitinen stereoadapter. The top edge of trapezoidal plate 88 also then should be in alignment with the top edge of horizontal bar 52A on the Laitinen stereoadapter, which provides a further check with respect to vertical and angular alignment of the positioning apparatus and Laitinen stereoadapter. The forward pin 92 and rear pin 96 are then advanced until the point 94 of pin 92 penetrates the patient's scalp and engages the skull and the blunt pad 100 on the end of pin 96 engages the scalp sufficiently firmly to prevent rotation of the positioning apparatus and stereotactic headring. Such adjustments of the forward and rear pins 92 and 96 are made while assuring that the trapezoidal plate 88 remains properly aligned with the bars 48, 50 and 52A of the stereoadapter.

The positioning apparatus 74 is so configured and dimensioned that, when it is thus aligned with the stereoadapter apparatus and rigidly attached to the patient's skull, the stereotactic headring 10 attached to the positioning apparatus will be so positioned that the coordinate system for the stereotactic headring will be substantially exactly aligned with the coordinate system for the stereoadapter apparatus. This is accomplished by configuring the positioning apparatus 74 so that it will support the stereotactic headring 10 in a position where the X, Y and Z axes of the stereotactic headring align with the X, Y and Z axes for the stereoadapter.

The X and Y axes of the Laitinen and BRW/CRW stereotactic systems already are substantially the same. By the design of the adapter, the lateral pins 82 align with the X axis and the pins 92, 96 align with the Y axis.

The zero point of the Z axis on the BRW/CRW system is by design 80 mm above the top surface of the BRW/CRW headring. The height of the vertical bars of the adapter preferably is designed so that, when properly applied, the top bar of the Laitinen stereoadpater lies 80 mm above the top surface of the BRW/CRW headring at the zero point of the Z axis. Aligning the zero point on the Z axis of the stereoadapter with the zero point on the Z axis for the stereotactic headring is accomplished by constructing the side brackets 80 so that they will support the top surface of the base 11 of headring 10 eighty mm below the zero point on the Z axis for the Laitinen stereoadapter coordinates. While this configuration preferably enables the X, Y and Z axes for the BRW/CRW stereotactic headring to substantially overlie the X, Y and Z axes for the Laitinen stereoadapter, it will be apparent to those skilled in the art that the selection of a zero point or zero plane for a cartesian coordinate system is a matter of choice and may be adjusted utilizing the software which creates and interprets the CAT scan, MRI, etc. diagnostic images. Thus, so long as the X, Y and Z axes for the BRW/CRW headring are angularly aligned with the X, Y and Z axes for the Laitinen stereoadapter, it is not absolutely required that the zero points on the X, Y and Z axes overlie each other, since selection of the zero point is a matter of convention and may change from system to system.

Figure 7:
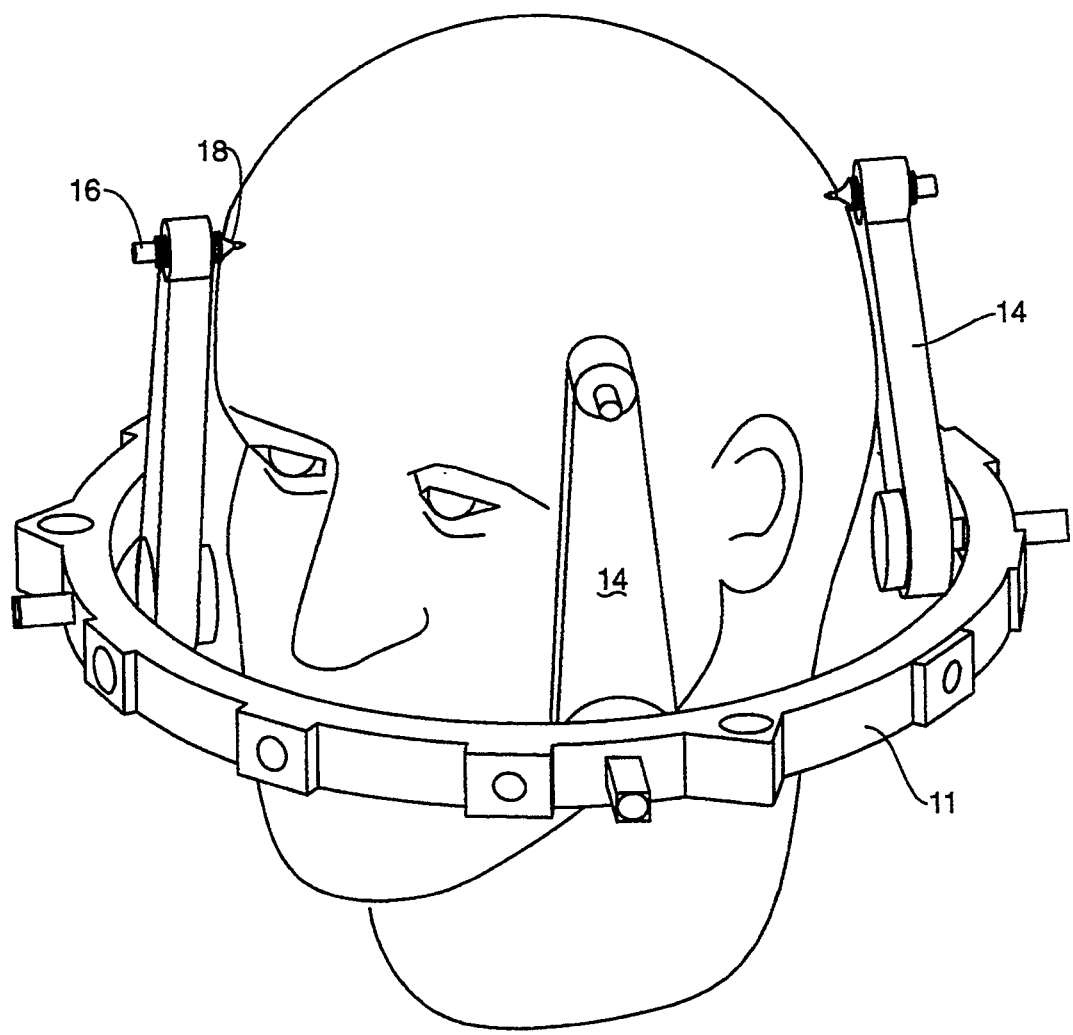
FIG. 7 (prior art) is an isometric view illustrating a patient's head with the BRW/CRW headring in place, following removal of the Laitinen stereoadapter and disengagement and removal of the positioning device of the present invention.

With the apparatus so aligned, the four adjustable pins 16 on the stereotactic headring 10 then may be advanced until the pin tips penetrate the patient's scalp and engage the skull, so that the stereotactic headring is rigidly affixed with respect to the patient's skull in proper alignment with the Laitinen stereoadapter 46. The positioning apparatus 74 and stereoadapter apparatus 46 then may be removed, leaving only the BRW/CRW stereotactic headring in place (FIG. 7) which then may be used by the physician for performing stereotactic intracranial surgery in the usual manner. Coordinates derived from earlier diagnostic scanning procedures performed utilizing the stereoadapter may be used for purposes of performing surgery or other treatment using the stereotactic headring, so positioned, and its associated attachments, appliances and instruments. In this manner, the noninvasive stereoadapter can be used for pre-operative planning studies and diagnostic procedures, thus eliminating the necessity for attaching the invasive stereotactic headring to the patient until the actual time of surgery.

Figure 8:
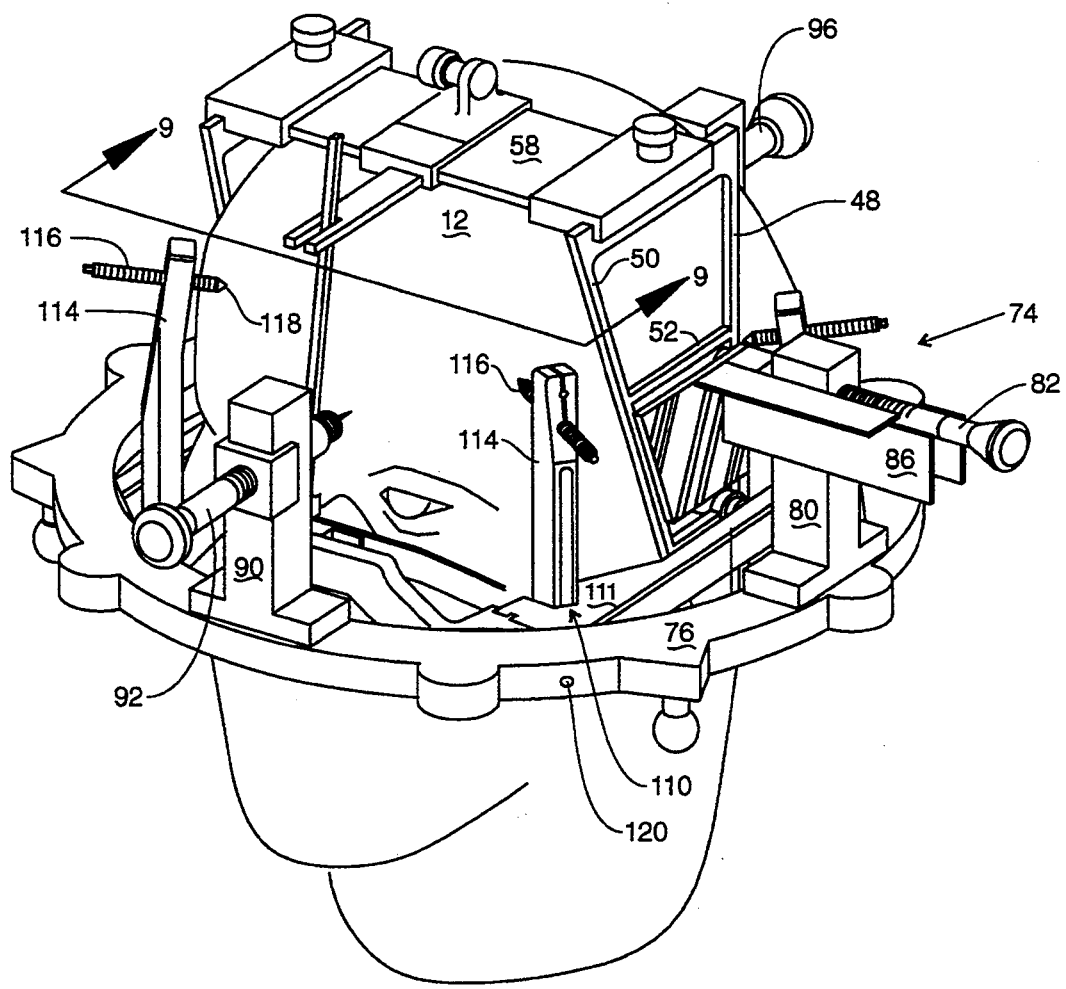
FIG. 8 is an isometric view of a patient's head fitted with a Laitinen stereoadapter apparatus as well as a Leksell stereotactic headring and with the positioning device of the present invention interrelating the positions of the Laitinen stereoadapter and Leksell headring.
Figure 9:
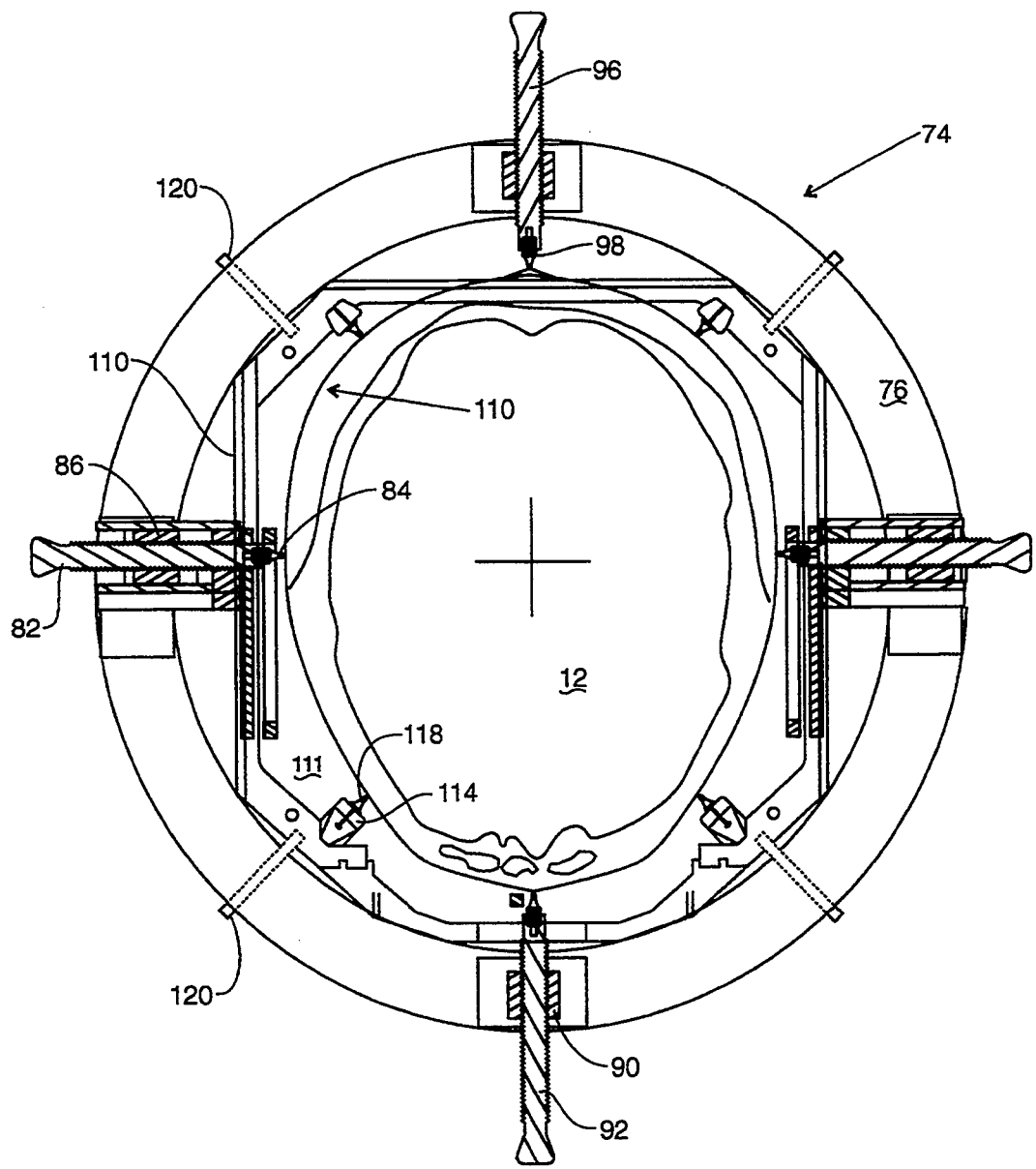
FIG. 9 is a plan view partly in section taken along line 9—9 of FIG. 8 and illustrating details of the Leksell headring and the positioning apparatus in accordance with the present invention.

Referring now to FIGS. 8 and 9, there is shown the positioning apparatus in accordance with the present invention used in conjunction with the headring 110 of a Leksell stereotactic system. The Leksell headring comprises a base 111 having an oblong central opening permitting the Leksell headring to be received in surrounding relationship to the patient's head. The outer perimeter of the Leksell headring 110 forms a polygonal, generally octagonal, shape. As shown, the inside diameter of the base 76 of the positioning apparatus of the present invention may be sized so as to accommodate the base 110 of the Leksell headring within the inside diameter of the positioning apparatus.

Like the BRW/CRW headring, the Leksell headring includes four vertical brackets 114 which extend upward from the base 111. Four adjustable pins 116 are threadedly engaged with the upper portions of the brackets. The pins 116 when rotated relative to the brackets 114, extend inwardly to engage the patient's skull, or retract outwardly to disengage from the patient's skull. The pins 116 have pointed tips or ends 118 which, when the pins are extended inwardly, penetrate the outer tissue of the patient's head 12 and engage the bone of the skull so as to rigidly and invasively affix the headring 110 to the skull. The pin tips or ends 118 may be removable and replaceable so as to reduce the possibility of spreading infection from one user of the headring apparatus to the next. Also, in certain applications where rigid positioning of the headring is less critical, noninvasive pads may be substituted for the pin tips 118, which permits the headring 110 to be engaged around the patient's head in a noninvasive manner.

Means are provided for releasably rigidly attaching the Leksell headring to the positioning apparatus 74. As illustrated in FIGS. 8 and 9, such means comprise four elongated pins 120 which extend through threaded openings in the base 76 of positioning apparatus 74 and into corresponding recesses in the base 111 of the Leksell headring 110. By extending or retracting threaded pins 120, the base of the Leksell headring can be attached to, or disengaged from, the base 76 of the positioning apparatus. Obviously, other means also could be used for releasably attaching a Leksell headring to the positioning apparatus 74.

As with the BRW/CRW-type headrings, the base 111 of the Leksell headring will, when supported from the positioning apparatus 74, have its X, Y and Z axes aligned with the X, Y and Z axes of the Laitinen adapter, whereby intracranial coordinates obtained from diagnostic procedures performed utilizing the Laitinen adapter may be utilized for treatment procedures performed utilizing the Leksell stereotactic system.

As previously described in connection with the BRW/CRW-type headring, once the Leksell headring is properly positioned by means of the positioning apparatus 74, in the same manner as described above in connection with the BRW/CRW headring, the four adjustable pins 116 on the Leksell headring then may be advanced until the pin tips penetrate the patient's scalp and engage the skull, so that the headring 110 is rigidly affixed with respect to the patient's skull in proper alignment with the Laitinen stereoadapter 46. The positioning apparatus 74 and stereoadapter apparatus 76 may then be removed, leaving only the Leksell headring in place, which then may be used by the physician for performing stereotactic surgery or other treatment or procedure in the usual manner. Like the BRW/CRW headring, the Leksell stereotactic system utilizes a variety of tools and attachments with the headring for holding and positioning surgical instruments and the like during surgical or treatment procedures.

The foregoing disclosure and description of the invention are illustrative only, and it will be apparent to those skilled in the art that various changes may be made in the size, shape, materials and other details of construction without departing from the scope of the invention, which is measured solely by the claims.

What is claimed is:

1. Positioning apparatus for interrelating the (1) positions of noninvasive stereoadapter apparatus used in performing a presurgical diagnostic procedure relating to a patient's intracranial area and (2) stereotactic apparatus used in performing a treatment procedure on said patient's intracranial area, said positioning apparatus comprising:
    a rigid base adapted to be received in substantially surrounding relationship to said stereoadapter apparatus,
    alignment means carried by said base for aligning said positioning apparatus in a known and reproducible relationship relative to a stereoadapter apparatus on the head of said patient;
    support means carried by said base for releasably rigidly supporting said positioning apparatus on said patient's head in surrounding relationship to said stereoadapter apparatus; and
    attachment means carried by said base for releasably attaching a stereotactic apparatus to said positioning apparatus,
    said positioning apparatus being so configured that when said positioning apparatus, with said stereotactic apparatus attached thereto, is disposed in surrounding relationship to said stereoadapter apparatus on said patient's head and said alignment means are suitably aligned with said stereoadapter apparatus, said stereotactic apparatus attached to said positioning apparatus will be so positioned with respect to said stereoadapter apparatus that coordinates established for said patient's intracranial areas utilizing said stereoadapter apparatus will be substantially aligned with the coordinates of said patient's intracranial areas established for said stereotactic apparatus, whereby diagnostic measurements made on said patient's intracranial areas utilizing said stereoadapter apparatus may be used for purposes of intracranial treatments performed utilizing said stereotactic apparatus.

2. The apparatus according to claim 1 wherein said rigid base of said positioning apparatus comprises a rigid ring.

3. The apparatus according to claim 1 wherein said support means comprise means for invasively and substantially rigidly engaging said positioning apparatus with said patient's skull.

4. The apparatus according to claim 1 wherein said support means comprise means for noninvasively and substantially rigidly engaging said positioning apparatus with said patient's head.

5. The apparatus according to claim 1 wherein said alignment means comprise a pair of substantially vertical, horizontally adjustable, plates configured to align with selected portions of said stereoadapter apparatus which serve as alignment indicia for said plates, so that when said plates on said positioning apparatus are adjusted to a position substantially adjacent to, and aligned with, said alignment indicia on said stereoadapter apparatus, said positioning apparatus will be properly aligned with respect to said stereoadapter apparatus.

6. The apparatus according to claim 1 wherein said support means comprise a plurality of elongated pins, each said pin being threadedly engaged with a support extending upwardly from said base, said pins being adapted, upon rotation, to extend into and retract out of engagement with said patient's head.

7. The apparatus according to claim 6 wherein at least some of said pins function also as alignment means for said positioning apparatus.

8. Positioning apparatus for interrelating the positions on a patient's head of (1) a stereoadapter adapted to be positioned on a patient's head and utilized in performing a diagnostic imaging procedure on the intracranial area of said patient's head, said diagnostic imaging procedure involving the application of a first set of spatial coordinates established for said intracranial area with respect to said stereoadapter and (2) a stereotactic headring to be utilized in performing a treatment procedure on said patient's intracranial area, said treatment procedure involving the application of a second set of spatial coordinates established for said intracranial area with respect to said stereotactic headring, said positioning apparatus comprising:
- a body formed of rigid material and adapted to be received in substantially surrounding relationship to said stereoadapter on said patient's head;
- alignment means on said body for aligning said positioning apparatus in a predetermined relationship with respect to said stereoadapter on said patient's head; and
- support means on said body for releasably rigidly supporting said positioning apparatus on said patient's head; and
- attachment means on said body for releasably rigidly attaching said stereotactic headring to said positioning apparatus,
- said positioning apparatus, including said body, alignment means, support means and attachment means, being so configured and dimensioned that, when said stereotactic headring is attached to said positioning apparatus by said attachment means and said positioning apparatus, with said stereotactic headring releasably attached thereto, is supported from said patient's head by said support means with said alignment means suitably aligned with said stereoadapter, said second set of spatial coordinates will be substantially aligned with said first set of spatial coordinates, whereby coordinates established for said patient's intracranial areas during said diagnostic imaging procedure utilizing said stereoadapter will be the same as the coordinates for said patient's intracranial areas utilizing said stereotactic headring.

9. The apparatus according to claim 8 wherein said body of said positioning apparatus comprises a rigid ring.

10. The apparatus according to claim 8 wherein said support means comprise means for invasively and substantially rigidly engaging said positioning apparatus with said patient's skull.

11. The apparatus according to claim 8 wherein said support means comprise means for noninvasively and substantially rigidly engaging said positioning apparatus with said patient's head.

12. The apparatus according to claim 8 wherein said alignment means comprise a pair of substantially vertical, horizontally adjustable, plates configured to align with selected portions of said stereoadapter apparatus which serve as alignment indicia for said plates, so that when said plates on said positioning apparatus are adjusted to a position substantially adjacent to, and aligned with, said alignment indicia on said stereoadapter apparatus, said positioning apparatus will be properly aligned with respect to said stereoadapter apparatus.

13. The apparatus according to claim 8 wherein said support means comprise a plurality of elongated pins, each said pin being threadedly engaged with a support extending upwardly from said body, said pins being adapted, upon rotation, to extend into and retract out of engagement with said patient's head.

14. The apparatus according to claim 13 wherein at least some of said pins function also as alignment means for said positioning apparatus.

15. The positioning apparatus according to claim 8 wherein said positioning apparatus is configured and dimensioned specifically to interact with a Laitinen steroadapter and a CRW stereotactic headring.

16. The positioning apparatus according to claim 8 wherein said positioning apparatus is configured and dimensioned specifically to interact with a Laitinen steroadapter and a Leksell headring.

17. A method for interrelating the position of, and coordinate system for, a stereoadapter apparatus used in performing a diagnostic procedure on a patient's intracranial area with the position of, and coordinate system for, a stereotactic apparatus used in performing a treatment procedure on said patient's intracranial area, said method comprising:
- substantially rigidly positioning said stereoadapter apparatus on said patient's head;
- providing a positioning apparatus including means for releasably attaching a stereotactic apparatus to said positioning apparatus, means for aligning said positioning apparatus, with said stereotactic apparatus attached thereto, in a known and reproducible relationship to said stereoadapter apparatus on said patient's head and support means for substantially rigidly supporting said positioning apparatus, with said stereotactic apparatus attached thereto, from said patient's head;
- attaching said stereotactic apparatus to said positioning apparatus;
- disposing said positioning apparatus, with said stereotactic apparatus attached thereto, in substantially surrounding relationship to said stereoadapter apparatus on said patient's head;
- aligning said alignment means on said positioning apparatus with said stereoadapter apparatus; and
- engaging said support means on said positioning apparatus with said patient's head while said alignment means on said positioning apparatus are suitably aligned with said stereoadapter apparatus,
- said resulting position of said stereotactic apparatus being effective to substantially exactly align a coordinate system established for use with said stereotactic apparatus with a coordinate system established for use with said stereoadapter apparatus, whereby diagnostic measurements made for said patient's intracranial area utilizing said stereoadapter apparatus may be used for purposes of performing treatment on said patient's intracranial area utilizing said stereotactic apparatus.

18. The method according to claim 17 comprising additionally the steps of
- invasively and substantially rigidly supporting said stereotactic apparatus on said patient's skull;
- disengaging said stereotactic apparatus from said positioning apparatus; and
- removing said positioning apparatus and said stereoadapter apparatus from said patient's head, while leaving said stereotactic apparatus engaged with said patient's head.

19. A method for interrelating the position of, and coordinate system for, a stereoadapter apparatus used in performing a diagnostic procedure on a patient's intracranial area with the position of, and coordinate system for, a stereotactic apparatus used in performing a treatment procedure on said patient's intracranial area, said method comprising:
- substantially rigidly positioning said stereoadapter apparatus on said patient's head;
- providing a positioning apparatus including means for releasably attaching a stereotactic apparatus to said positioning apparatus, means for aligning said positioning apparatus in a known and reproducible relationship relative to a stereoadapter apparatus on said patient's head and means for substantially rigidly supporting said positioning apparatus on said patient's head;

disposing said stereotactic apparatus and said positioning apparatus in substantially surrounding relationship to said stereoadapter apparatus on said patient's head;

aligning said alignment means on said positioning apparatus with said stereoadapter apparatus; and engaging said support means on said positioning apparatus with said patient's head while said alignment means on said positioning apparatus are suitably aligned with said stereoadapter apparatus; and attaching said stereotactic apparatus to said positioning apparatus, a resulting position of said stereotactic apparatus relative to said patient's head being effective to substantially exactly align a coordinate system established for use with said stereotactic apparatus with a coordinate system established for use with said stereoadapter apparatus, whereby diagnostic measurements made for said patient's intracranial area utilizing said stereoadapter apparatus may be used for purposes of performing treatment on said patient's intracranial area utilizing said stereotactic apparatus.

20. The method according to claim 19 comprising additionally the steps of invasively and substantially rigidly supporting said stereotactic apparatus on said patient's skull;

disengaging said stereotactic apparatus from said positioning apparatus; and removing said positioning apparatus and said stereoadapter apparatus from said patient's head, while leaving said stereotactic apparatus engaged with said patient's head.

* * * * *